(12) United States Patent
Rasche et al.

(10) Patent No.: US 7,277,565 B2
(45) Date of Patent: Oct. 2, 2007

(54) METHOD OF RECONSTRUCTING A HIGH-RESOLUTION 3D IMAGE

(75) Inventors: Volker Rasche, Hamburg (DE); Michael Grass, Hamburg (DE)

(73) Assignee: Koninklijke Philips Electronics, N.V., Eindhoven (NL)

( * ) Notice: Subject to any disclaimer, the term of this patent is extended or adjusted under 35 U.S.C. 154(b) by 713 days.

(21) Appl. No.: 10/481,808

(22) PCT Filed: Jun. 13, 2002

(86) PCT No.: PCT/IB02/02267

§ 371 (c)(1), (2), (4) Date: Dec. 22, 2003

(87) PCT Pub. No.: WO02/103639

PCT Pub. Date: Dec. 27, 2002

(65) Prior Publication Data

US 2004/0175024 A1    Sep. 9, 2004

(30) Foreign Application Priority Data

Jun. 20, 2001 (DE) .................................. 101 29 631

(51) Int. Cl.
*G06K 9/00* (2006.01)

(52) U.S. Cl. .................... 382/128; 382/154; 382/254

(58) Field of Classification Search ................ 382/103, 382/107, 128, 129, 130, 131, 132, 133, 134, 382/154, 236, 254, 285; 600/415, 420; 128/916
See application file for complete search history.

(56) References Cited

U.S. PATENT DOCUMENTS

| 6,073,042 | A  | * | 6/2000 | Simonetti ..................... 600/420 |
| 6,252,979 | B1 | * | 6/2001 | Lee et al. .................... 382/133 |
| 6,556,695 | B1 | * | 4/2003 | Packer et al. ................ 382/128 |
| 6,714,668 | B1 | * | 3/2004 | Kerrien et al. .............. 382/130 |

* cited by examiner

*Primary Examiner*—Samir Ahmed
*Assistant Examiner*—Abolfazl Tabatabai

(57) ABSTRACT

The invention relates to a method of reconstructing a high-resolution 3D image (G) of an examination zone of a patient from a 3D image data set (D) of the examination zone, the examination zone being subject to a periodic motion which is measured, in parallel with the acquisition of the 3D image data set (D), as a motion signal (E) which represents the periodic motion. In order to enable the formation of high-resolution 3D images having an enhanced image quality, the invention proposes a method of this kind which includes the following steps:
a) reconstructing a number of low-resolution 3D images (I) from the 3D image data set (D), the low-resolution 3D images (I) being reconstructed from 3D image data of the 3D image data set (D) which has been acquired during different phases of motion of the periodic motion,
b) determining motion information (B) of at least one sub-zone (A) of the examination zone during the different phases of motion by means of the low-resolution 3D images (I),
c) selecting a temporal reconstruction window (T) in which the motion of the at least one sub-zone (A) is below a predetermined level,
d) reconstructing a high-resolution sub-image (K) for the at least one sub-zone (A) from 3D image data (D) lying in the temporal reconstruction window (T) selected for the sub-zone (A), and
e) forming the desired 3D image (G) from the at least one sub-image (K), the zones of the 3D image (G) which are not reconstructed as sub-images then being reconstructed from the 3D image data so as to be combined with the at least one sub-image (K).

9 Claims, 2 Drawing Sheets

METHOD OF RECONSTRUCTING A HIGH-RESOLUTION 3D IMAGE

BACKGROUND

Figure 1:
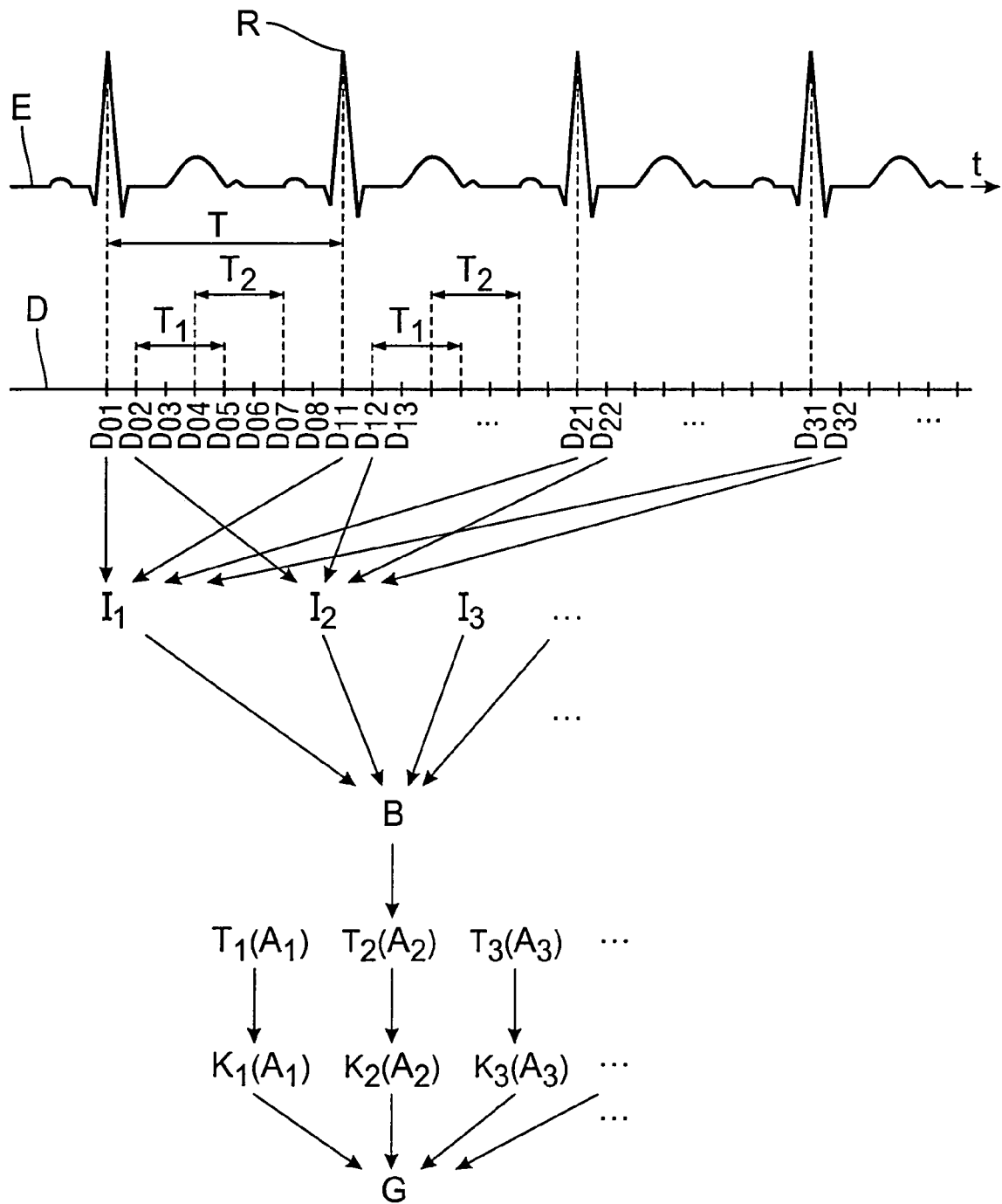

The invention relates to a method and a device for the reconstruction of a high-resolution 3D image of an examination zone of a patient from a 3D image data set of the examination zone, the examination zone being subject to a periodic motion which is measured, in parallel with the acquisition of the 3D image data set, as a motion signal which represents the periodic motion.

A method and a device of this kind are known. The reconstruction of 3D images of moving objects, for example, of the heart of a patient, is nowadays carried out by selecting a suitable temporal reconstruction window in which acceptable results can be achieved for the overall anatomy to be imaged. This means that from the 3D image data set acquired that 3D image data which has been acquired in a given time window in which, for example, the anatomy to be imaged has been subject to the least motion, is selected for the reconstruction. In the case of a periodic motion of the anatomy, for example, the cardiac motion or the respiratory motion, therefore, only 3D image data from a given phase of motion are used for the reconstruction, whereas all other reconstruction data acquired is not evaluated. For the imaging of the heart or the coronary vessels, for example, it is preferred to use exclusively 3D image data acquired during the diastole, whereas the formation of 3D images of the abdomen utilizes exclusively 3D data which has been acquired in the state of exhalation.

The motion of given parts of organs or notably of different parts of the heart, however, does not take place simultaneously but follows the excitation pattern of the organ; this means that individual parts of the organ to be imaged can move to a different extent at different instants. The use of a fixed (temporal) reconstruction window for the entire object to be imaged, therefore, often gives rise either to a degraded image quality or to sub-optimum use of the data acquired during the assumed phases of rest of the organ.

SUMMARY

Therefore, it is an object of the invention to enhance the method and the device of the kind set forth in such a manner that high-resolution 3D images of a moving examination zone of a patient can be formed with an enhanced image quality.

This object is achieved in accordance with the invention by means of a method as disclosed by an embodiment of the invention and by means of a device as disclosed in another aspect of the invention. The method is characterized in that it includes the following steps:

a) reconstructing a number of low-resolution 3D images from the 3D image data set, the low-resolution 3D images being reconstructed from 3D image data of the 3D image data set which has been acquired during different phases of motion of the periodic motion, b) determining motion information of at least one sub-zone of the examination zone during the different phases of motion by means of the low-resolution 3D images, c) selecting a temporal reconstruction window in which the motion of the at least one sub-zone is below a predetermined level, d) reconstructing a high-resolution sub-image for the at least one sub-zone from the 3D image data lying in the temporal reconstruction window selected for the sub-zone, and e) forming the desired 3D image from the at least one sub-image, the zones of the 3D image which are not reconstructed as sub-images then being reconstructed from the 3D image data so as to be combined with the at least one sub-image.

Another embodiment of the invention discloses the corresponding device which is provided with a reconstruction unit as well as an arithmetic unit in order to carry out the method.

The invention is based on the recognition of the fact that for the reconstruction of a 3D image it is less than optimum to use only 3D image data from the same temporal zone, that is, from a fixed phase of motion, for the entire examination zone, for example, an organ to be examined such as the heart. Because individual parts of the examination zone could move to a different extent at different instants or in different phases of motion, in accordance with the invention it is proposed to select specific reconstruction windows for the individual parts of the examination zone which move differently, to reconstruct sub-images in such reconstruction windows, and to combine said sub-images subsequently so as to form an overall image, that is, the desired 3D image. Each individual sub-image can thus be derived from different 3D image data of the same 3D image set.

The complete examination zone to be reproduced in a 3D image can thus be subdivided into individual sub-zones for which a respective optimum (temporal) reconstruction window is determined each time in accordance with the invention. However, individual sub-zones of the examination zone which are of particular interest can also be selected in order to perform such a formation of sub-images therein on the basis of an adapted reconstruction window, whereas all other zones of the examination zone are reconstructed in the conventional manner on the basis of all 3D image data of the 3D image data set or on the basis of a special sub-quantity thereof which was acquired in a low-motion phase.

Further versions and preferred embodiments of the method and the device in accordance with the invention are disclosed in other embodiments of the invention. The invention is particularly suitable for use in the reconstruction of 3D images of the heart as well as of the coronary vessels; in that case the motion signal representing the periodic cardiac motion preferably corresponds to an electrocardiogram. The invention, however, in principle can also be used for the imaging of other objects or other zones, for example, for the imaging of the abdomen or of individual organs such as the liver or the stomach, because such zones or organs are also subject to a periodic motion, that is, the respiratory motion. A respiratory motion signal can then be measured as the motion signal; various methods are suitable for this purpose, for example, a signal which represents the motion of the abdominal wall or of the diaphragm. Carrying out the invention in principle offers an enhanced image quality, notably when individual sub-zones or sub-objects of the examination zone to be imaged exhibit a non-simultaneous pattern of motion.

According to a preferred version of the invention, a motion model of the examination zone is formed in order to determine the motion of the at least one sub-zone; to this end, notably significant points in the low-resolution 3D images are tracked or objects reproduced in the low-resolution 3D images are segmented. Significant points may be, for example, anatomical features such as, for example, bifurcations in the coronary vessels. Tracking such significant points in time in the individual low-resolution sub-images thus enables the acquisition of motion information on how said points have moved in time. Alternatively, this motion information can be automatically extracted by way of segmentation, for example, of the vascular tree in the low-resolution 3D images associated with various phases of motion.

According to a further preferred version a separate temporal reconstruction window is selected for each volume element of the examination zone or for regions of the examination zone which are of particular interest, each volume element (voxel) or the regions of special interest being separately reconstructed on the basis of the 3D image data acquired in the selected temporal reconstruction window. In as far as adequate calculation time is available, or if a 3D image with the highest possible resolution and the best possible motion correction is to be formed, the method in accordance with the invention can thus be applied to every individual voxel of the examination zone; this means that for each individual voxel there is derived motion information on the basis of which a special temporal reconstruction window is determined for the voxel, that is, a window in which the reconstruction of this voxel image value takes place. However, it is also possible to combine each time several voxels so as to form individual groups of voxels for which the method in accordance with the invention is carried out so as to save calculation time.

The invention can be used in principle for the formation of a 3D image from arbitrary 3D image data; this means that in principle it is not important which modality is used to acquire the 3D image data. The method in accordance with the invention, however, is preferably used in conjunction with 3D image data acquired by means of computed tomography or by means of a 3D rotation X-ray method, for example, by means of a C-arm X-ray system.

The invention also relates to a computer program as disclosed in another embodiment of the invention for the execution of a method and/or for controlling a device as described herein. This computer program includes notably programming means which are suitable for carrying out the method in accordance with the invention or for controlling the device in accordance with the invention when the computer program is executed by a computer or a suitable arithmetic unit.

DRAWINGS

Figure 2:
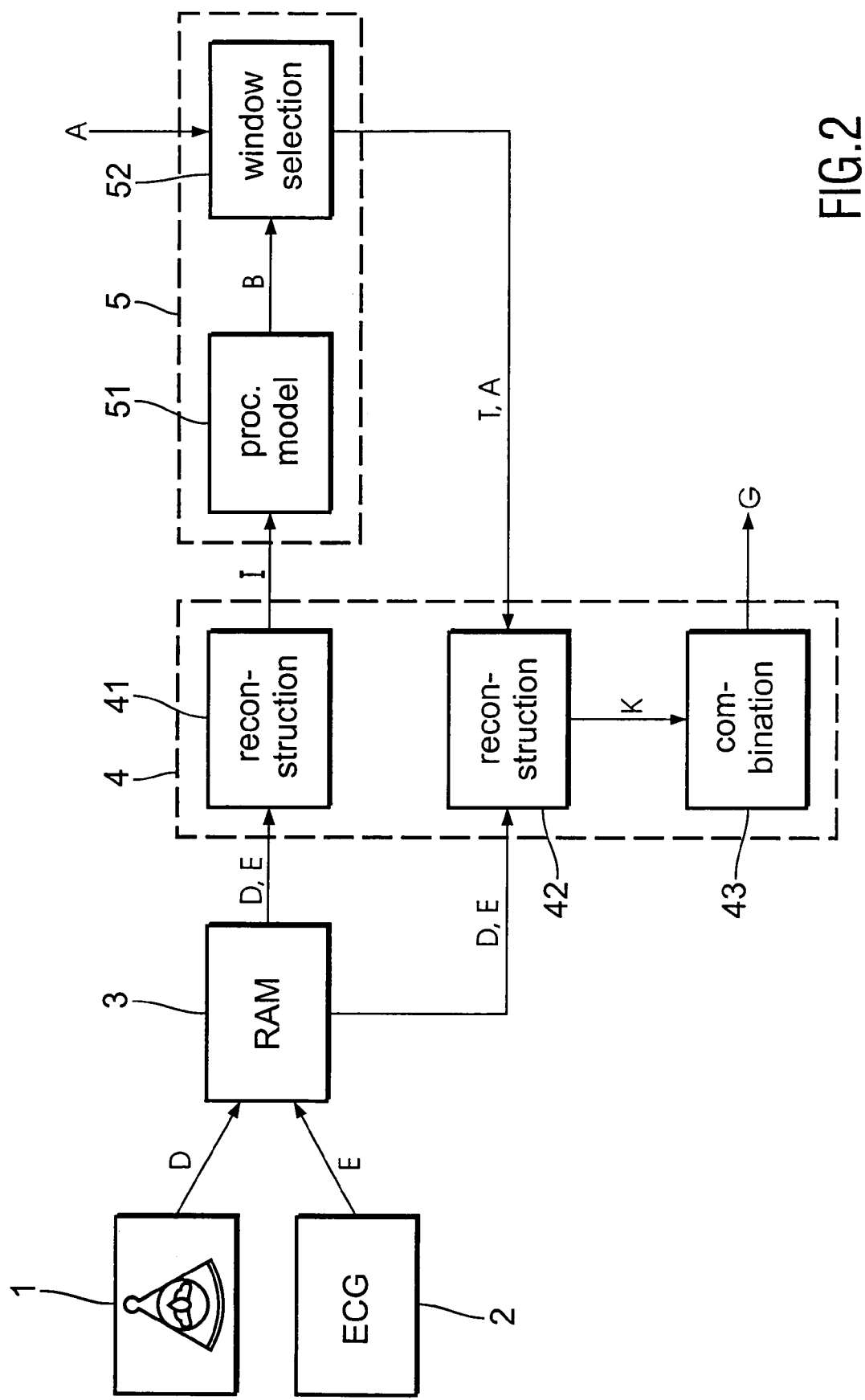

The invention will be described in detail hereinafter with reference to the drawings. Therein:

FIG. 1 is a diagrammatic representation illustrating the method in accordance with the invention, and FIG. 2 shows a block diagram illustrating a device in accordance with the invention.

DESCRIPTION

The method in accordance with the invention will be described in detail hereinafter on the basis of an example where a high-resolution 3D image of the vascular tree of the coronary vessels is to be reconstructed. When the contraction pattern of the heart is studied, it appears that this pattern commences with the contraction of the atria, followed by the contraction of the ventricles, starting with the apex. Because of the complex motion pattern of the anatomy observed, the various volume elements (voxels) along the coronary artery exhibit significantly different patterns of motion during the cardiac rhythm or a cardiac motion phase. Whereas in the known reconstruction method the temporal reconstruction window is defined in a simple manner by a constant temporal delay in respect of the R deflection in the electrocardiogram (ECG) and a given temporal length of the reconstruction window. The same reconstruction window is then used for the reconstruction of all voxels in the volume to be reconstructed.

In accordance with the invention, however, voxel-specific reconstruction windows are to be selected; these windows are used first for the reconstruction of individual sub-images which are subsequently combined so as to form a desired overall image. FIG. 1 shows an electrocardiogram E which shows the characteristic variation as a function of time t of a motion signal representing the cardiac motion (a voltage is measured). A significant aspect of the ECG is the so-called R deflection which will be used hereinafter so as to define the reconstruction windows.

Using an imaging system, for example, a computed tomography apparatus or a C-arm X-ray device operating on the principle of 3D rotation angiography, first a 3D image data set D is acquired. This means that individual data set elements, that is, so-called projections $D_{01}, D_{02}, \ldots$, of the examination zone are acquired from different perspectives or imaging positions, that is, continuously in time t and at equidistant instants. These individual image data set elements together form a 3D image data set D wherefrom a 3D image of the examination zone can be formed. Because the acquisition of the 3D image data D takes place temporally in parallel with the acquisition of the ECG E, the 3D image data D acquired can be assigned to individual phases of motion of the examination zone. The data set elements $D_{01}$, $D_{11}, D_{21}, D_{31}, \ldots$ have thus all been acquired in a first phase of motion in which the ECG E exhibits the R deflection; the data set elements $D_{02}, D_{12}, D_{22}, D_{32}, \ldots$ have been acquired in a second phase of motion with a first, fixed temporal delay with respect to the R deflection, etc. The R deflections occur at a distance in time (period) amounting to T.

In accordance with the invention respective low-resolution 3D images I are formed from the data set elements acquired each time during the same phase of motion. This means that, for example, a first low-resolution image $I_1$ is reconstructed from the data set elements $D_{01}, D_{11}, D_{21}$, $D_{31}, \ldots$ of the first phase of motion, that a second low-resolution image $I_2$ is reconstructed from the data set elements $D_{02}, D_{12}, D_{22}, D_{32}, \ldots$ of the second phase of motion, etc. Each of these low-resolution images $I_1, I_2$, $I_3, \ldots$ is thus formed from 3D image data exhibiting a fixed temporal delay relative to the R deflection.

From such low-resolution 3D images $I_1, I_2, I_3, \ldots$ there is derived motion information B which provides information on the motion of the anatomy present in the examination zone during the cycle of motion. In the example described herein, therefore, motion information B is to be acquired as to how individual zones of the heart or individual coronary vessels move during the cardiac cycle. To this end, for example, significant points such as bifurcations of the coronary vessels can be tracked in the individual low-resolution images I or the vascular tree can be automatically segmented in these images. It is thus possible to derive information defining the phases of motion in which sub-zones of the examination zone, or in an extreme case individual voxels of the examination zone, have moved and to what extent and also the phases of motion or periods of time in which no or only insignificant motion has occurred during a motion cycle.

This motion information is subsequently used to determine a respective optimum temporal reconstruction window $T_1$, $T_2$, $T_3$, . . . for individual sub-zones $A_1$, $A_2$, $A_3$, . . . , which may also correspond to individual voxels in an extreme case. For a first sub-zone $A_1$ a first temporal reconstruction window $T_1$ is thus determined; this means at the same time that only image data set elements acquired from this segment of time of the motion cycle are used for the reconstruction of a high-resolution sub-image $K_1$ of this sub-zone $A_1$. This reconstruction window $T_1$ can also be recognized in FIG. 2; it can be deduced therefrom that, for example, the reconstruction of a high-resolution sub-image $K_1$ of the sub-zone $A_1$ utilizes only the image data set elements $D_{02}$, $D_{03}$, $D_{04}$, $D_{05}$, $D_{12}$, $D_{13}$, $D_{14}$, $D_{15}$, $D_{22}$, $D_{23}$, . . . because this sub-zone obviously has not been subject to motion, or only hardly so, during the time window $T_1$ of the motion cycle. For a second sub-zone $A_2$, however, a different temporal reconstruction window $T_2$ is derived from the motion information B. For the formation of a high-resolution image $K_2$ of the sub-zone $A_2$, therefore, image data set elements $D_{04}$, $D_{05}$, $D_{06}$, $D_{07}$, $D_{14}$, $D_{15}$, . . . . are used, because obviously the sub-zone $A_2$ has moved the least during the segment of time $T_2$.

For each sub-zone A for which the method in accordance with the invention is to be used, therefore, an individual temporal reconstruction window T is selected, the temporal delay relative to the R deflection and the duration in time of the reconstruction window may be different for each sub-zone A. The reconstruction windows, however, may overlap or also be identical.

As has already been described, in an extreme case a separate temporal reconstruction window T can be determined for each individual voxel of the examination zone, so that each individual voxel is optimally reconstructed individually from specially selected data set elements. In another extreme case a separate reconstruction window may be determined for a single sub-zone only of the examination zone, whereas all other zones of the examination zone are reconstructed in a customary manner from all 3D image data of the 3D image data set D or from 3D image data of a fixed temporal reconstruction window. It is to be noted again that the reconstruction windows are variable and cover for each sub-zone a different length and a different segment in time of the motion period.

In a final step the high-resolution sub-images $K_1$, $K_2$, $K_3$, . . . formed are combined so as to form the desired high-resolution 3D image G. The sub-zones in this 3D image for which a separate reconstruction window was selected in accordance with the invention thus exhibit a clearly enhanced image quality with a higher resolution and fewer artifacts.

FIG. 2 is a representation in the form of a block diagram of a device in accordance with the invention for carrying out the described method. Therein, first a 3D image data set D is acquired by means of an image data acquisition device 1, for example, a computed tomography, apparatus or a C-arm X-ray device. In parallel therewith a motion signal E, for example, an ECG is acquired by means of a suitable measuring device 2, for example, by means of an electrocardiograph; this motion signal provides information as regards the motion of the anatomy to be imaged. The data acquired is first stored in a memory 3 and subsequently applied to the reconstruction unit 4 for evaluation and further processing.

Therein, the low-resolution 3D images I, representing the examination zone in different phases of motion, are formed first in a first reconstruction module 41. Subsequently, said low-resolution images are applied to an arithmetic unit 5 in which the motion information B, for example, in the form of a motion model, is acquired in a first module 51; this motion information is subsequently evaluated in a second module 52. In the module 52, therefore, the motion information is used to determine the individual temporal reconstruction windows T for individual sub-zones A which are defined, for example by a user. These reconstruction windows are then applied to a second reconstruction module 42 which forms the respective high-resolution sub-images K for the individual sub-zones A on the basis of this information and as well as on the basis of the motion signal E from the 3D image data set. These high-resolution sub-images K are ultimately combined in a combination module 43 so as to form the desired high-resolution 3D overall image G of the examination zone.

The invention claimed is:

1. A method of reconstructing a high-resolution 3D image (G) of an examination zone of a patient from a 3D image data set (D) of the examination zone, the examination zone being subject to a periodic motion which is measured, in parallel with the acquisition of the 3D image data set (D), as a motion signal (E) which represents the periodic motion, which method includes the steps of:
   a) reconstructing a number of low-resolution 3D images (1) from the 3D image data set (D), the low-resolution 3D images (I) being reconstructed from 3D image data of the 3D image data set (D) which has been acquired during different phases of motion of the periodic motion,
   b) determining motion information (B) of at least one sub-zone (A) of the examination zone during the different phases of motion by means of the low-resolution 3D images (I),
   c) selecting a temporal reconstruction window CT) in which the motion of the at least one sub-zone (A) is below a predetermined level,
   d) reconstructing a high-resolution sub-image (E) for the at least one sub-zone (A) from 3D image data (D) lying in the temporal reconstruction window (T) selected for the sub-zone (A), and
   e) forming the desired 3D image (G) from the at least one sub-image (K), the zones of the 3D image (G) which are not reconstructed as sub-images then being reconstructed from the 3D image data so as to be combined with the at least one sub-image (K).

2. A method as claimed in claim 1, wherein a motion model of the examination zone is formed in order to determine the motion information (B) of the at least one sub-zone (A), that is, notably by tracking significant points in the low-resolution 3D images or by segmentation of objects reproduced.

3. A method as claimed in claim 1, wherein for each voxel of the examination zone, or for regions of the examination zone which are of particular interest, there is selected a separate temporal reconstruction window (T), and that each volume element or each region of particular interest, is separately reconstructed on the basis of the 3D image data acquired in the selected temporal reconstruction window (T).

4. A method as claimed in claim 1, wherein the 3D image data set (D) has been acquired by means of a computed tomography apparatus or a 3D rotation X-ray device.

5. A method as claimed in claim 1, wherein an electrocardiogram or a respiratory motion signal is used as the motion signal (E) representing the motion of the examination zone.

6. A computer program stored on a computer readable medium for carrying out the method claimed in claim 1.

7. A device for reconstructing a high-resolution 3D image (G) of an examination zone of a patient from a 3D image data set (D) of the examination zone, the examination zone being subject to a periodic motion which is measured, in parallel with the acquisition of the 3D image data set (D), as a motion signal (E) which represents the periodic motion, which device includes
   a) a reconstruction unit (4) for the reconstruction of a number of low-resolution 3D images (I) from the 3D image data set (D), the low-resolution 3D images (I) being reconstructed from 3D image data of the 3D image data set (D) which has been acquired during different phases of motion of the periodic motion,
   b) an arithmetic unit (5) for determining the motion of at least one sub-zone (A) of the examination zone during the different phases of motion by means of the low-resolution 3D images (1), the arithmetic unit being arranged to select a temporal reconstruction window (T) in which the motion of the at least one sub-zone (A) is below a predetermined level, and the reconstruction unit (4) being arranged to reconstruct at least one high-resolution sub-image (K) for the at least one sub-zone (A) from 3D image data (D) lying in the temporal reconstruction window (T) selected for the sub-zone (A), and to form the desired 3D image (G) from the at least one sub-image (K), the zones of the 3D image (G) which are not reconstructed as sub-images then being reconstructed from the 3D image data so as to be combined with the at least one sub-image (K).

8. A device for forming 3D images of an examination zone of a patient which includes an image acquisition device (1) for the acquisition of a 3D image data set of the examination zone, the examination zone being subject to a periodic motion, and also includes a measuring device (2) for measuring, in parallel with the acquisition of the 3D image data set, a motion signal which represents the periodic motion, and also a device for the reconstruction of a high-resolution 3D image as claimed in claim 6.

9. A device as claimed in claim 8, wherein the device is a computed tomography apparatus or a 3D rotation X-ray device, notably a C-arm X-ray device.

* * * * *